United States Patent
Bruder et al.

(10) Patent No.: US 8,524,973 B2
(45) Date of Patent: Sep. 3, 2013

(54) WOUND AND THERAPY COMPRESS AND DRESSING

(75) Inventors: Mark H. Bruder, Alpharetta, GA (US);
Aaron N. Ingram, Canton, GA (US)

(73) Assignee: Bruder Healthcare Company, Alpharetta, GA (US)

( * ) Notice: Subject to any disclaimer, the term of this patent is extended or adjusted under 35 U.S.C. 154(b) by 0 days.

(21) Appl. No.: 10/380,803

(22) PCT Filed: Sep. 17, 2001

(86) PCT No.: PCT/US01/28908
§ 371 (c)(1),
(2), (4) Date: May 30, 2003

(87) PCT Pub. No.: WO02/22060
PCT Pub. Date: Mar. 21, 2002

(65) Prior Publication Data
US 2003/0208150 A1    Nov. 6, 2003

Related U.S. Application Data

(60) Provisional application No. 60/232,826, filed on Sep. 15, 2000.

(51) Int. Cl.
*A61F 5/00* (2006.01)
(52) U.S. Cl.
USPC .............. 602/48; 602/2; 602/53; 607/108
(58) Field of Classification Search
USPC ............ 602/48, 41–43, 2, 46; 604/304–308; 424/443–449; 128/888, 889; 607/108–112, 607/96
See application file for complete search history.

(56) References Cited

U.S. PATENT DOCUMENTS

| | | | |
|---|---|---|---|
| 2,066,271 A | | 12/1936 | Irwin |
| 3,013,982 A | * | 12/1961 | Breck et al. ................ 252/181.6 |
| 4,525,410 A | * | 6/1985 | Hagiwara et al. ............ 428/198 |
| 4,775,585 A | | 10/1988 | Hagiwara et al. |
| 4,826,497 A | * | 5/1989 | Marcus et al. ................ 604/359 |

(Continued)

FOREIGN PATENT DOCUMENTS
EP    0691113    10/1996

*Primary Examiner* — Kim M Lewis
(74) *Attorney, Agent, or Firm* — Gardner Groff Greenwald & Villanueva, PC

(57) ABSTRACT

The invention provides a wound dressing or therapy compress (100) containing a fill material (108) permanently loaded with an antimicrobial silver. The dressing or compress comprises a flexible upper backing (104) and a lower shell (102) fastened to one another, and each of which comprises a synthetic fabric. The lower shell is fluid-permeable and is adapted to be placed in direct or covered contact with a wound or tissue to be treated. The backing may be either fluid permeable or non-permeable, as desired, to allow for the release or retention of moisture. The shell and backing are joined to one another to form a plurality of fill material enclosures (106) therebetween, each such fill material enclosure containing a zeolite fill material which is permanently loaded with antimicrobial silver. The presence of the silver within the fill material promotes a germ and microbial free environment approximate the shell and within the dressing or compress. So constructed, the dressing or compress may be used to cover and protect a wound while absorbing exudate, and may also provide and maintain a heated and/or a moist environment to promote the healing of wounds.

33 Claims, 4 Drawing Sheets

(56) References Cited

U.S. PATENT DOCUMENTS

| | | | |
|---|---|---|---|
| 4,906,466 A | 3/1990 | Edwards et al. | |
| 4,919,648 A | 4/1990 | Sibalis | |
| 5,019,254 A * | 5/1991 | Abrevaya et al. | 210/616 |
| 5,028,435 A | 7/1991 | Katz et al. | |
| 5,123,900 A * | 6/1992 | Wick | 602/41 |
| RE34,692 E | 8/1994 | Becher | |
| 5,409,472 A | 4/1995 | Rawlings et al. | |
| 5,413,788 A | 5/1995 | Edwards et al. | |
| 5,846,559 A | 12/1998 | Hopp | |
| 5,890,487 A * | 4/1999 | Kimmel | 128/845 |
| 5,900,258 A | 5/1999 | Engler | |
| 5,977,428 A * | 11/1999 | Bozigian et al. | 602/48 |
| 6,045,820 A * | 4/2000 | Messier | 424/443 |
| 6,353,145 B1 * | 3/2002 | Church | 602/48 |

\* cited by examiner

WOUND AND THERAPY COMPRESS AND DRESSING

CROSS REFERENCE TO RELATED APPLICATIONS

This application claims priority to, and the benefit of the filing date of U.S. patent application Ser. No. 60/232,826, filed on Sep. 15, 2000, in the United States Patent and Trademark Office.

FIELD OF THE INVENTION

The present invention relates in general to moist-heat therapy wound dressings and compresses. More particularly, the present invention relates to a wound dressing or compress containing antimicrobial silver providing a germ and microbial free environment within the article.

BACKGROUND OF THE INVENTION

Modern wound dressings are designed to promote healing by providing a moist, warm or heated, wound environment. Warming a wound promotes healing by increasing blood flow to the area. Moisture in a wound is also very important to the healing process because it helps cells grow and divide, and reduces scarring. Available modern dressings may be dampened or moistened and then heated, for example, by microwave heating. Concurrent with the development of these dressings is the concern regarding a potential for microbial colonization of the wound. Antibiotics are available to combat infections but many people are allergic to certain antibiotics and antibiotic usage can cause gastrointestinal upset or other side effects. Further, excessive use of antibiotics has been blamed for the occurrence of treatment-resistant bacteria.

Moist heat therapy applied by an area compress may also be beneficial to the treatment of arthritic or sprained joints, strained muscles, back pain, rheumatoid arthritis, or in any treatment where heat might be applied through or to the skin to promote circulation therein and thereunder. In such applications where no wound exudates contaminate therapy materials, reusability of the compress is an attractive cost-efficient design feature. Bacterial presence can cause dermatological problems to the treated area and further, a growing microbial colony in a reusable compress can cause the spread of infection through cross contamination when handled. This may represent a particular threat to therapy patients, many of whom have persistent or slow-healing injuries or compromised immunity systems.

A growing strategy for reducing the potential for infection or bacterial growth in a wound or on skin tissue under moist heat therapy is the incorporation of noble metal antimicrobials into the therapeutic wound dressing. The most prevalent such metal in use is silver due to its relative lack of cytotoxic effects and wide spectrum of antimicrobial effectiveness. Medical materials and instruments are available which provide the emission of silver metal or silver compounds to provide an antimicrobial effect. Such available dressings, once moistened, release silver into the surrounding liquid. The dressing thereby becomes an effective antimicrobial barrier. The silver, however, is consumed and lost in the process. Such products are inherently not conveniently reusable.

In both moist heat therapy wound dressings and compresses, bacterial and fungal growth can also cause unpleasant odor and unsightly discoloration which may adversely affect the morale of the patient. Thus there is a need in general for dressings and compresses designed to maintain sterility therein and to also provide microbial free moisture.

SUMMARY OF THE INVENTION

The present invention comprises a wound dressing or therapy compress having a granular fill material permanently loaded with at least one antimicrobial agent. The at least one antimicrobial agent comprises a form of silver, which form of silver may comprise atomic silver or a composition of silver. The dressing or compress thus comprises a fluid permeable shell and a backing, each of which is attached to the other to define a plurality of fill enclosures therebetween, and a fill material enclosed within the respective enclosures. A fluid permeable outer cover may be provided to protect the dressing or compress. The dressing may be used to shelter and protect a wound while absorbing exudate, and may also provide and maintain a heated and/or moist environment to promote the healing of the wound. The compress may be used to deliver moist heat therapy to an arthritic or sprained joint or strained muscle area.

The fill material may be prepared wet or moistened, or desiccated to dryness to either deliver or absorb moisture as appropriate to the desired treatment. The fill material absorbs or delivers this moisture through the lower shell. The shell is formed to be fluid-permeable, i.e., vapor-permeable and liquid-permeable, and is adapted to be placed in contact with a wound or tissue directly or through a vapor-permeable and liquid-permeable outer cover. The backing may also be fluid-permeable, or non-permeable if so desired, so as to allow for the release or retention of moisture as appropriate to the desired treatment.

The shell and backing are joined to form at least one, and preferably a plurality of enclosures therebetween. The enclosures may contain the loaded fill material. The presence of the antimicrobial agent within all or some of the fill material promotes a germ and microbial free environment at and near the lower shell and within the dressing or compress. The dressing or compress may be washable and reusable.

DETAILED DESCRIPTION OF THE INVENTION

Figure 1:
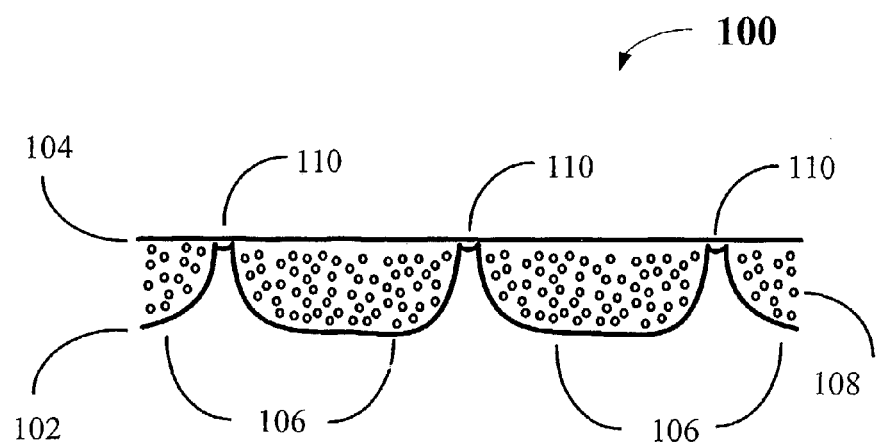
FIG. 1 is a partial side cross-sectioned view of the dressing or compress of the present invention.

Referring now to FIGS. 1-4, and as best illustrated in FIG. 1, a dressing or compress 100 is illustrated having a lower shell 102 and a flexible upper backing 104 which are joined or otherwise fastened to one another to form a series of enclosures 106 therebetween. The enclosures are provided for the containment and relatively uniform distribution of a plurality of fill granules 108 placed therein.

The enclosures may be fashioned as filled pods which are draped from the backing. The shell 102 forms the contact surface of the dressing or compress used to drape or form the bottom of the filled enclosures which are to be placed against the tissue to be treated, and to conform to the shape of the treatment area. The backing forms the smoother outer surface of the dressing or compress facing away from the treatment area.

Figure 2:
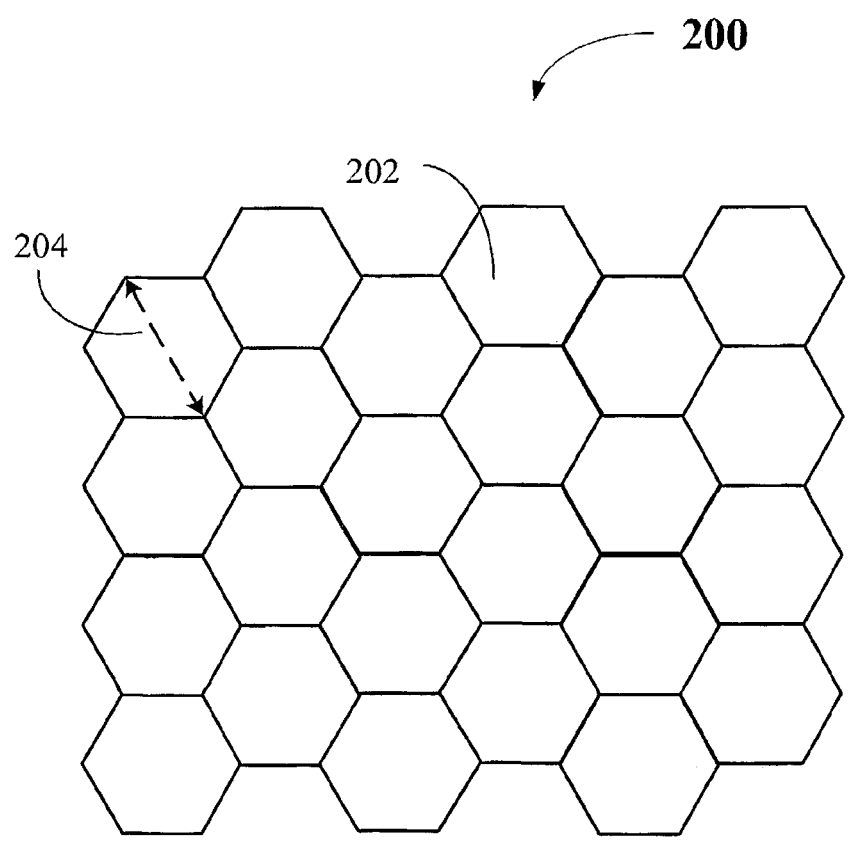
FIG. 2 is partial plan view of an exemplary hexagonal enclosure pattern.

The enclosures 106 may be defined as hexagons using patterned seams 110 for local symmetry and efficient regular plane division. An illustrative hexagonal pattern 200 of enclosures 202 is illustrated in FIG. 2. The enclosures might also be fashioned as circles, octagons, or of any desired shape as may be appropriated for the desired treatment. The enclosures may be selectively sized as appropriate to the application. Each hexagonal shaped enclosure 202 has a lengthwise dimension 204 extending from a first corner to an opposite second corner thereof. For example, and not by way of limitation, this dimension may be in the range of from approximately one inch to approximately four inches in length. Large treatment areas such as the human torso or appendages may best be served with enclosures having a dimension 204 extending lengthwise for approximately 4 inches. Highly contoured areas such as the face may best be served with enclosures having a dimension 204 of approximately 1 inch in length.

Figure 3:
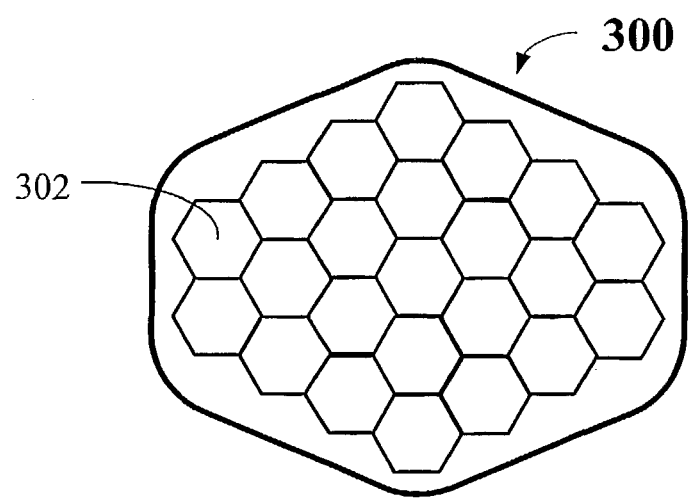
FIG. 3 is a plan view of an alternate exemplary dressing or compress with a hexagonal enclosure pattern.
Figure 4:
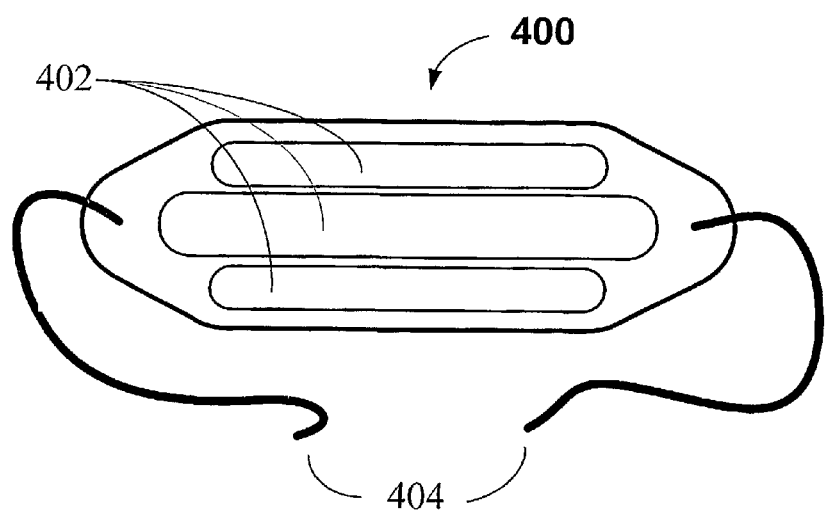
FIG. 4 is a plan view of a wrap compress with ties using the dressing or compress of the present invention.

An alternate dressing or compress 300 is illustrated in FIG. 3, having a plurality of hexagonal patterned enclosures 302. Each of the enclosures may also be formed as a channel-like rectangle, as illustrated in FIG. 4. The embodiment of the dressing or compress 400 is formed to have several channel enclosures 402 formed within a wrap compress having securing ties 404. So constructed, the dressing or compress 400 may be provided for the treatment of soreness or strains of the human back.

The size of the enclosures and overall dressing are selected to serve the desired treatment. Selected single sites for treatment such as the eye may best be treated using a single enclosure dressing or compress appropriately sized and shaped to rest comfortably in the eye hollow of the human face. The dressing or compress may be shaped as a regular or irregular polygon, any smooth closed curve, or any closed combination of line segments and smooth curves. The invention is not limited to constructions conforming to or only serving the human body. The invention provides a potentially useful treatment for the ailments of mammals and any animals benefiting from the healing properties of moisture and/or heat therapy.

A fluid-permeable, i.e., a vapor-permeable and/or a liquid-permeable protective outer cover (not illustrated) may be provided to encompass the compress. This may be preferable to limit contamination of the dressing or compress. For the treatment of open wounds, an uncovered disposable dressing (not illustrated) may be preferred for optimal formable contact with, and healing of, the exposed tissues.

The fill contained within the enclosure or enclosures may comprise a synthetic porous crystalline granular aluminosilicate zeolite, commonly used as a molecular sieve material, or other substances with similar properties. The fill material may further comprise other inert additives and physical matrices without affecting the antimicrobial and hydrous efficacies of the fill. Silver loading of the fill may be attained by the process of ion-exchange, as known. In this process, a solution containing atomic silver or a composition of silver bathes, or is passed through, a bed of the fill granules 108 (FIG. 1). An ion-exchange column method, as known in the art, may be performed in which an aqueous solution containing atomic silver or a composition of silver may be passed through a column bed of the fill granules, and the eluted solution may again be passed through the bed or may receive additional silver and then be again passed through the bed.

Various ion-exchange schedules known in the art may be applied to produce retention of the silver. The final content by weight of the atomic silver or silver composition may be as high as twenty percent of the final loaded fill granules. The loaded fill granules produced by ion-exchange will exhibit high retention of the silver even under subsequent exposure to fluids and microwave irradiation. The fill granules may comprise a blend of both loaded and unloaded zeolite or a substance retaining silver. The presence of the atomic silver or silver composition will not interfere with the useful properties of the fill granules such as the moisture desorption and adsorption properties which may be desirable in the use of the dressing or compress. The inherent hydrophilic nature of the zeolite provides that a substantial water content is available therein by absorption from the atmosphere. The water so absorbed may be sufficient, or may be supplemented by manually added water, for providing the microwave responsive water content of the dressing or compress. The compositions of silver used may include but are not limited to, silver compounds, and silver salts such as silver chloride and silver nitrate.

The presence of the silver within the fill granules contained in the enclosure of the invention provides anti-microbial properties to the dressing or compress. The ion-exchange loaded fill granules will retain the silver despite microwave heating as may be required in the use of the dressing or compress, which prevents the release of silver into a treated wound if the invention is used as a dressing. Further, the retention of the silver within the fill granules provides assured antimicrobial performance in a reusable and potentially washable, if so desired, moist heat therapy compress.

In the described embodiments of the invention, the lower shell and the upper backing are each constructed of materials known in the art. Each may therefore be comprised of multi-layered laminates, for example, with pore sizes selectable to meet the moisture transmission and retention properties desired for the specific treatment sought. The dressing or compress is adapted to be placed and to remain in intimate contact with the area to be treated to maintain a heated and/or moist environment thereabout. Dressing or compress constructions using woven textiles of natural fibers have been found to have limited spatial conformance to the various shapes, dimples, wrinkles and joints offered by the human body, although these materials may be used if so desired.

Accordingly, preferred dressing or compress constructions will use formable woven and non-woven synthetic materials or combinations thereof which may include, but are not limited to, synthetic olefin, polyester, urethane, and nylon. The shell and the backing may be fastened together across the area of the dressing or compress with a fill material, the fill granules 108, received therebetween. The shell and the backing may be fastened to one another by methods which may include, but are not limited to, adhesive attachment, RF welding, ultra-sonic attachment, sewing, or patterned heat application using a template or forming die to form a seal. To provide for the secure placement of the dressing or compress, peripheral or attachment fastening devices may be included which may comprise the desired number of VELCRO®, hook and loop fasteners, adhesives, high tactility polymer materials, and/or material ties.

Throughout the construction of the dressing or compress, attention and care is taken in the selection of materials regarding thermal response to microwave heating. For design simplicity, all synthetic, microwave non-responsive materials may be selected to provide that the fill and/or water content of a moistened dressing or compress provide the only substantial thermal response to microwave irradiation.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the invention. Moreover, although specific terms are employed herein, they are used only in a generic and descriptive sense, and not for the purposes of limiting the described invention. The words "a," "an," or "the" can mean one or more, depending upon the context in which the words are used hereinabove.

We claim:

1. A moist therapy antimicrobial dressing and compress for treatment of a treated body part of a patient, said article comprising:
    a flexible backing;
    a shell for application to the treated body part of the patient, the shell being attached to the backing to form at least one enclosure between the backing and the shell; and
    a plurality of fill granules loosely contained within each of said at least one enclosure for delivery of moist heat therapy from the fill granules to the treated body part of the patient, said fill granules not bound in the backing or the shell, and the fill granules comprising hydrophilic zeolite molecular sieve particles retaining at least one form of silver therein;
    and wherein the hydrophilic zeolite molecular sieve particles substantially retain said silver therein upon multiple exposures to microwave irradiation, but allow repeated absorption and dissipation of moisture to and from the hydrophilic zeolite material for delivery of moist heat therapy to the treated body part of the patient.

2. The article of claim 1, wherein the backing and the shell each comprise a synthetic microwave non-responsive fabric.

3. The article of claim 2, wherein the backing and the shell are each separately selected from the group of synthetic fabrics consisting of synthetic olefin, polyester, urethane, and nylon.

4. The article of claim 1, wherein the shell is fluid permeable.

5. The article of claim 4, wherein the shell is vapor permeable.

6. The article of claim 4, wherein the shell is liquid permeable.

7. The article of claim 1, wherein the shell is attached to the backing by a sewn fiber.

8. The article of claim 1, wherein the shell is attached to the backing by an RF weld.

9. The article of claim 1, wherein the shell is attached to the backing by an ultrasonic weld.

10. The article of claim 1, wherein the shell is attached to the backing by an adhesive.

11. The article of claim 1, wherein the shell is attached to the backing by a heat induced seal.

12. The article of claim 1, wherein the at least one enclosure is formed to define a geometric shape.

13. The article of claim 12, wherein the geometric shape is selected from the group of geometric shapes consisting of a circle, an ellipse, a channel, and a hexagon.

14. The article of claim 1, wherein the at least one enclosure is formed as a polygon.

15. The article of claim 1, wherein the at least one enclosure is shaped as a hexagon having a lengthwise dimension extending from a first corner to a spaced second corner thereof, said dimension being in the range of from approximately one inch to four inches in length.

16. The article of claim 1, said at least one enclosure comprising a plurality of enclosures spaced with respect to one another and which together substantially cover a predetermined area of the article.

17. The article of claim 1, wherein the hydrophilic zeolite material comprises an ion exchange material.

18. The article of claim 1, wherein the at least one form of silver is selected from the group consisting of atomic silver, silver compounds, silver salts, silver chloride, and silver nitrate.

19. The article of claim 1, wherein the hydrophilic zeolite material contains moisture absorbed from the atmosphere.

20. The article of claim 19, wherein the hydrophilic zeolite material and moisture content have a thermal response to microwave irradiation.

21. The article of claim 1, wherein the hydrophilic zeolite material contains moisture absorbed from the atmosphere.

22. The article of claim 21, wherein the hydrophilic zeolite material and moisture content have a thermal response to microwave irradiation.

23. The article of claim 1, wherein the hydrophilic zeolite material substantially retains said silver therein upon multiple exposures to fluids.

24. The article of claim 1, wherein the backing and the shell are each comprised of microwave non-responsive fabric.

25. The article of claim 1, wherein said hydrophilic zeolite material comprises a porous zeolite.

26. The article of claim 25, wherein said porous zeolite comprises an aluminosilicate zeolite.

27. A moist therapy antimicrobial dressing or compress for treatment of a treated body part of a patient, said article comprising:
    a flexible backing;
    a fluid-permeable shell for application to the treated body part of the patient, the fluid-permeable shell being attached to the flexible backing to form at least one enclosure; and
    a plurality of fill granules loosely contained within each of said at least one enclosure for delivery of moist heat therapy from the fill, granules through the fluid-permeable shell to the treated body part of the patient shell, the fill granules comprising hydrophilic zeolite particles retaining at least one form of silver therein; and wherein the hydrophilic zeolite particles substantially retain said silver therein upon multiple exposures to microwave irradiation, but allow repeated absorption and dissipation of moisture to provide moist heat therapy through the fluid-permeable shell to the treated body part of the patient.

28. The article of claim 27, wherein the backing and the shell are each comprised of at least one synthetic microwave non-responsive fabric.

29. The article of claim 27, wherein said at least one form of silver is selected from the group consisting of atomic silver, silver compounds, silver salts, silver chloride, and silver nitrate.

30. The article of claim 27, wherein the hydrophilic zeolite material substantially retains said silver therein upon mulitiple exposures to fluids.

31. The article of claim 27, wherein the backing and the shell are each comprised of microwave non-responsive fabric.

32. The article of claim 27, wherein said hydrophilic zeolite comprises aluminosilicate.

33. A moist therapy compress for treatment of a treated body part of a patient, said compress comprising an outer shell for application to the treated body part of the patient, the outer shell formed of a flexible, fluid-permeable material, said shell formed to comprise at least one pod; and a plurality of granules of porous zeolite material loosely contained within each of said at least one pods for delivery of moist heat therapy from the fill granules, through the outer shell, and to the treated body part of the patient, the granules of porous zeolite material being loaded with a silver by ion exchange, whereby the silver is retained within the granules of porous zeolite material throughout repeated absorption and dissipation of moisture in delivering moist heat therapy to the treated body part of the patient, and throughout repeated microwave heating.

* * * * *